US00PP37519P3

(12) United States Plant Patent
Bull

(10) Patent No.: US PP37,519 P3
(45) Date of Patent: Jul. 7, 2026

(54) ***ECHINACEA* PLANT NAMED 'BullEchipur 119'**

(50) Latin Name: *Echinacea purpurea*
Varietal Denomination: BullEchipur 119

(71) Applicant: Hartwig Bull, Gönnebek (DE)

(72) Inventor: Hartwig Bull, Gönnebek (DE)

( * ) Notice: Subject to any disclaimer, the term of this patent is extended or adjusted under 35 U.S.C. 154(b) by 0 days.

(21) Appl. No.: 19/235,130

(22) Filed: Jun. 11, 2025

(65) Prior Publication Data

US 2025/0386750 P1 Dec. 18, 2025

Related U.S. Application Data

(60) Provisional application No. 63/731,837, filed on Jun. 12, 2024.

(51) Int. Cl.
*A01H 5/02* (2018.01)
*A01H 5/12* (2018.01)
*A01H 6/14* (2018.01)

(52) U.S. Cl.
USPC ..... Plt./428
CPC ..... *A01H 6/1448* (2018.05); *A01H 5/02* (2013.01); *A01H 5/12* (2013.01)

(58) Field of Classification Search
USPC ..... Plt./428
CPC ..... A01H 5/02; A01H 5/00; A01H 6/1448; A01H 6/14
See application file for complete search history.

(56) References Cited

U.S. PATENT DOCUMENTS

| | | | | |
|---|---|---|---|---|
| 7,982,110 | B2 | 7/2011 | Ren | |
| PP31,064 | P2 | 11/2019 | Ren et al. | |
| PP35,164 | P2 | 5/2023 | Ren | |
| PP35,286 | P3 * | 7/2023 | Bull | A01H 6/1448 Plt./428 |

OTHER PUBLICATIONS

Brookgreen Gardens *Echinacea purpurea* 'Pas702918' retrieved on Aug. 27, 2025 at https://www.brookgreen.org/plant-collection/name/echinacea-purpurea-pas702918-powwow%25C2%25AE-white, 3 pp. (Year: 2025).*

Wist et al.Floral Structure and Dynamics of Nectar Production in *Echinacea pallida* var. *angustifolia* (*Asteraceae*), Int. J. Plant Sci. 169(6):708-722, 2008 (Year: 2008).*

ThinkPlants Catalog, 2024-2025, retrieved on Sep. 4, 25 at https://online.flippingbook.com/view/530070179/34/, 6 pages.

* cited by examiner

*Primary Examiner* — June Hwu
(74) *Attorney, Agent, or Firm* — The Webb Law Firm

(57) ABSTRACT

A new and distinct variety of *Echinacea* plant named 'BullEchipur 119' having large white flowers, good growth habit, uniform growth, good branching habit, and good propagation rates.

1 Drawing Sheet

Botanical classification: *Echinacea purpurea.*
Varietal denomination: 'BULLECHIPUR 119'.

BACKGROUND OF THE INVENTION

The present invention relates to a new and distinct cultivar of *Echinacea*, botanically known as *Echinacea purpurea*, and hereinafter referred to by the name 'BullEchipur 119'.

The new *Echinacea* was discovered by the Inventor in August 2021, in a controlled environment in Gönnebek, Germany, as a part of a planned breeding program. The new *Echinacea* was selected on the basis of its large white flowers, good growth habit, uniform growth, good branching habit, and good propagation rates.

Asexual propagation of the new cultivar by in vitro culture since September 2021, in Gönnebek, Germany, has shown that the unique features of this new *Echinacea* are stable and reproduced true to type in successive generations.

SUMMARY OF THE INVENTION

The following traits have been repeatedly observed and are determined to be unique characteristics of 'BullEchipur 119'. These characteristics in combination distinguish 'BullEchipur 119' as a new and distinct cultivar:

1. Compact growth
2. White flowers
3. Lots of large flowers
4. More branching habit
5. Uniform growth
6. Nice green leaves
7. Fast crop time
8. Early flowering In side-by-side comparisons conducted by the Inventor in Gönnebek, Germany, plants of the new *Echinacea* differed from plants of the female parent, 'Bul-2020-05' of *Echinacea purpurea*, in the following characteristics:

1. More compact
2. Larger white flowers
3. Good branching
4. Clean green leaves, where clean refers to the consistency of the color (i.e. clean means the leaves have no brown spots or necroses)
5. Earlier flowering In side-by-side comparisons conducted by the Inventor in Gönnebek, Germany, plants of the new *Echinacea* differed from plants of the male parent, 'Bul-2020-09' of *Echinacea purpurea*, in the following characteristics:

1. More compact
2. More vivid and larger flowers
3. More branches
4. Lots of flowers
5. Earlier flowering Plants of the new *Echinacea* can be compared to the plants of the *Echinacea* cultivar 'PAS702918' which uses the trade name 'PowWow® White', believed to be unpatented. In side- by-side comparisons conducted by the Inventor in Gönnebek, Germany, plants of the new *Echinacea* differed from plants of the cultivar 'PowWow® White' in the following characteristics:

1. More compact
2. More branching habit
3. Very even growth
4. More flowers
5. Nice cleaner leaves (specifically, less brown spots and necroses)
6. Earlier flowering

DESCRIPTION OF THE DRAWINGS

The accompanying colored photographs illustrate the overall appearance of the new *Echinacea*, showing the colors as true as it is reasonably possible to obtain in colored reproductions of this type. Colors in the photographs may differ slightly from the color values cited in the detailed botanical description, which accurately describes the colors of the new *Echinacea*.

FIG. 1 comprises a top perspective view of a typical plant of 'BullEchipur 119' under natural light.

DESCRIPTION OF THE PLANT

The cultivar *Echinacea* has not been observed under all possible environmental conditions. The phenotype may vary somewhat with variations in environment such as temperature and light intensity without, however, any variance in genotype.

The aforementioned photographs and following observations and measurements describe plants of the new *Echinacea* that were grown in an outdoor nursery in Gönnebek, Germany. During the production of the plants, temperatures averaged about 18-20° C. Plants used for the photographs and description were about 22 weeks from planting. Color references are made to The Royal Horticultural Society Colour Chart, 2015 version, except where general terms of ordinary dictionary significance are used.

PLANT

Botanical classification: *Echinacea purpurea.*

Parentage: 'Bul-2020-05' and 'Bul-2020-09'.

Propagation:

*Time to initiate roots.*—About 7 days.

*Time to develop roots.*—About 40-50 days.

*Time to produce a finished flowering plant.*—About 12-14 weeks.

*Root description.*—Lots of roots, free-branching, nice, healthy-looking root system.

Plant description:

*Growth rate/vigor.*—Time to grow young plant: About 8-10 weeks. Time from young plant to flowering: About 10-12 weeks.

*Plant habit.*—Compact/upright.

*Plant height.*—45-50 cm.

*Plant width.*—35-40 cm.

*Branching habit.*—Lots of branches, upright.

*Lateral branches.*—Number per plant: 13-20. Length: 2-35 cm. Diameter: 3-8 mm. Angle: Upright, outward. Strength: Strong. Texture: Pubescent. Color: 146C. Internode length: 1-5 cm.

*Foliage.*—Stem Leaves: Length: Youngest Leaves: Approximately 3 cm. Fully Expanded Leaves: 8-12 cm on average. Width: 1-7 cm. Shape: Lanceolate. Shape of Apex: Acuminate. Shape of Base: Attenuate to Acute. Orientation and aspect: Straight to curved. Texture: Upper surface: Rough. Lower surface: Rough. Young leaves: Upper surface color: 137A. Lower surface color: 137C. Fully expanded leaves: Upper surface color: 137A. Lower surface color: 137C. Venation: Type: Cross venulate to longitudinal. Color: Upper surface: 145A. Lower surface: 145B. Rugosity: Weak to Medium. Margin: Entire. Basal Leaves: Length: Approximately 20 cm. Width: 1-7 cm. Shape: Lanceolate. Shape of Apex: Acuminate. Shape of Base: Attenuate to Acute. Orientation and aspect: Straight to curved. Texture: Upper surface: Rough. Lower surface: Rough. Young leaves: Upper surface color: 137A. Lower surface color: 137C. Fully expanded leaves: Upper surface color: 137A. Lower surface color: 137C. Venation: Type: Cross venulate to longitudinal. Color: Upper surface: 145A. Lower surface: 145B. Rugosity: Weak to Medium. Margin: Entire.

Flowers:

*Bud.*—Stage of opening: Single type blossom. Shape: Elliptic sharpened ray florets and tubular disk floret. Diameter: 1-3.5 cm. Length: 1.2-2.5 cm. Color: 137C.

*Natural flowering season.*—10-12 weeks after planting.

*Inflorescence.*—Form: Single flower. Disc and ray floret arrangement: Single composite flower. Average number per plant: 12-18. Average number per branch: 1-3. Fragrance: None. Diameter: 4-10 cm. Height: 2-4 cm. Diameter of disc: 1.5-4 cm. Receptacle height: 1 cm. Receptacle diameter: 1.5-4 cm. Ray florets: Number per inflorescence: 15-22. Arrangement: In two to three whorls. Length: 1.5-4.4 cm. Width: 0.9-1.6 cm. Shape: Ellipse. Shape of Apex: Obtuse with shallow (approximately 1 mm) indentations. Shape of Base: Acute. Margin: Entire. Texture: Upper surface: Smooth, glabrous. Lower surface: Rough. Color: When opening: Upper surface: 155C. Lower surface: 155C. At maturity: Upper surface: 155C. Lower surface: 155C. Ground color description: White. Attitude: Horizontal. Profile in Cross Section: Weakly Concave. Disc florets: Average Height when Matured: 12 mm. Number per inflorescence: Numerous, too many to quantify. Arrangement: In center of receptacle. Length: 8-15 mm. Width: 1-2 mm. Shape: Tubular. Shape of Apex: Sharp. Color of receptacle spine with receptacle bracts: Immature: 146C. At maturity: 153C. Phyllaries: Number per inflorescence: 35-50. Arrangement: In 3-4 whorls. Length: 0.5-1.5 cm. Width: 2-3 mm. Shape: Lanceolate. Shape of Apex: Elongate, oval. Shape of Base: Fused. Margin: Entire. Texture: Upper surface: Rough. Lower surface: Rough.

Color: Immature: Upper surface: NN137C. Lower surface: NN137C. At maturity: Upper surface: NN137C. Lower surface: NN137C.

Reproductive organs:

*Androecium*.—Presence: On disk florets. Number: One. Filament: Length: 1-2 mm. Color: 153C. Anther: Shape: Oval. Length: 1 mm. Color: 153C. Pollen: Color: 15B. Amount: Too much to quantify.

*Gynoecium*.—Presence: In disk and ray florets. Pistil length: 1-2 mm. Stigma: Shape: Two-parted. Color: 153C. Style: Length: 1-2 mm. Color: 153C.

*Seeds/fruit*.—Length: 1-2 mm. Color: 164C.

Disease/pest resistance:

*Disease resistance*.—No additional disease resistance has been observed beyond the typical resistance in *Echinacea* plants.

*Pest resistance*.—No additional pest resistance has been observed beyond the typical resistance in *Echinacea* plants.

Weather tolerance:

*Temperature tolerance*.—No additional temperature resistance has been observed beyond the typical resistance in *Echinacea* plants.

*Drought tolerance*.—No additional drought resistance has been observed beyond the typical resistance in *Echinacea* plants.

I claim:

1. A new and distinct cultivar of *Echinacea* plant named 'BullEchipur 119', as herein illustrated and described.

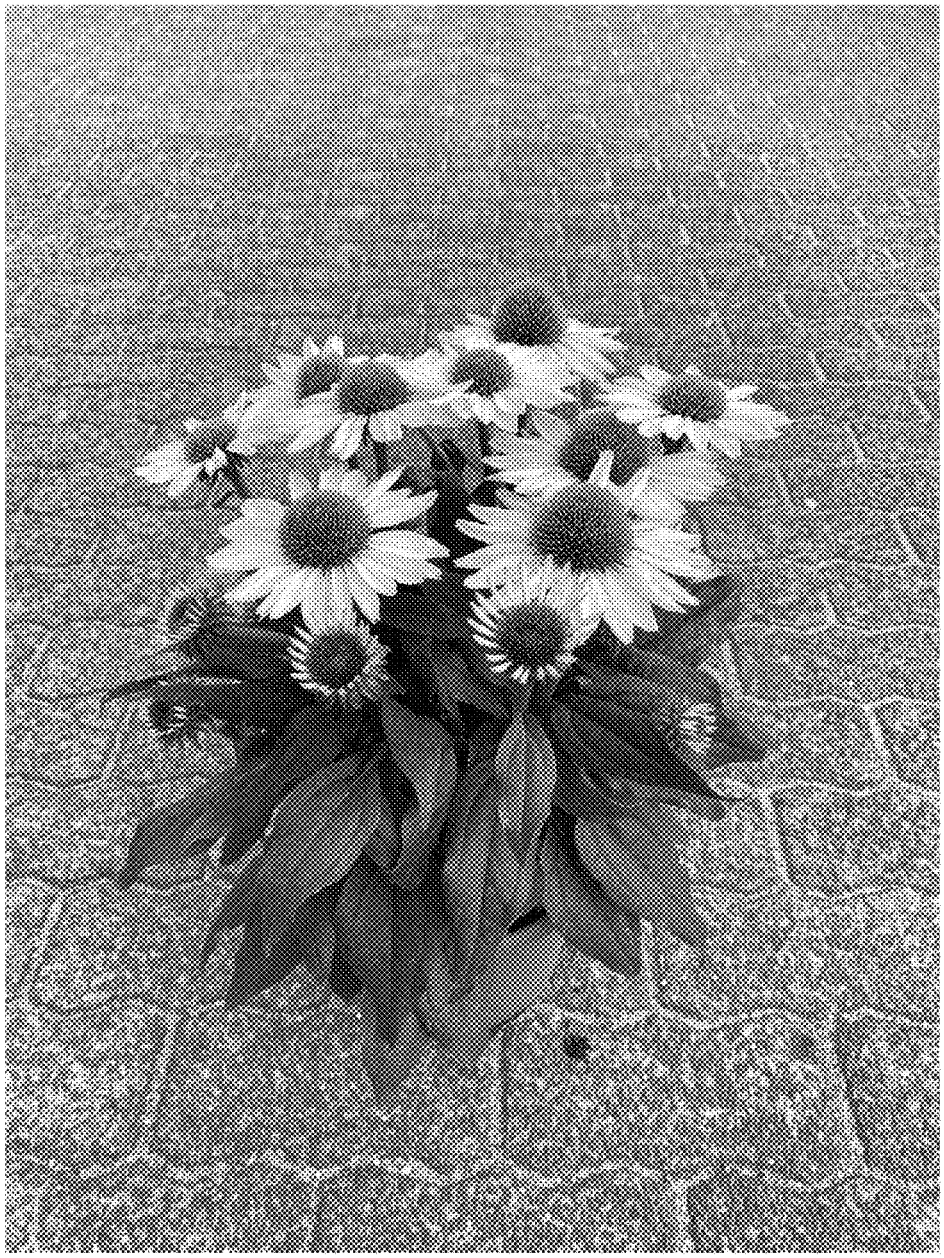

* * * * *